United States Patent [19]

Toriya et al.

[11] 4,225,729

[45] Sep. 30, 1980

[54] PROCESS FOR HYDROGENATION OF DIACETOXYBUTENE

[75] Inventors: Jun Toriya; Ken Shiraga, both of Kurashiki; Takeru Onoda; Akihisa Ohno, both of Yokohama, all of Japan

[73] Assignee: Mitsubishi Chemical Industries, Limited, Tokyo, Japan

[21] Appl. No.: 747,018

[22] Filed: Dec. 2, 1976

Related U.S. Application Data

[63] Continuation of Ser. No. 562,980, Mar. 28, 1975, abandoned.

[30] Foreign Application Priority Data

Mar. 28, 1974 [JP] Japan .................................. 49-34844

[51] Int. Cl.$^3$ ..................... C07C 67/283; C07C 69/16
[52] U.S. Cl. .................................... 560/263; 560/244
[58] Field of Search ............... 260/491, 690, 699, 700; 560/263

[56] References Cited

U.S. PATENT DOCUMENTS 4,010,197 3/1977 Toriya et al. ......................... 260/491

FOREIGN PATENT DOCUMENTS 1170222 11/1969 United Kingdom ..................... 260/491

OTHER PUBLICATIONS

Groggins, Unit Processes in Org. Syn., 1958, pp. 611 & 643.

*Primary Examiner*—Vivian Garner
*Attorney, Agent, or Firm*—Oblon, Fisher, Spivak, McClelland & Maier

[57] ABSTRACT

Diacetoxybutane is prepared by a process for hydrogenating diacetoxybutene in the presence of a supported hydrogenation catalyst comprising catalytically reacting diacetoxybutene with hydrogen continuously in an insulation reaction apparatus utilizing a fixed-bed of said hydrogenation catalyst, withdrawing the reaction effluent continuously from said reaction apparatus, circulating at least a part of said reaction effluent to said reaction apparatus while controlling the temperature of influx of said reaction apparatus at a temperature lower than the temperature of efflux from said reaction apparatus by 5° to 100° C.

10 Claims, 2 Drawing Figures ial scale, it is very important to keep the reaction
PROCESS FOR HYDROGENATION OF DIACETOXYBUTENE This is a continuation of application Ser. No. 562,980, filed Mar. 28, 1975, now abandoned.

BACKGROUND OF THE INVENTION

1. Field of the Invention

The present invention relates to a process for hydrogenation of diacetoxybutene. More particularly, the present invention relates to a process for hydrogenating diacetoxybutene which has been prepared by the acetoxylation reaction of butadiene in the presence of a supported hydrogenation catalyst.

2. Description of the Prior Art

Diacetoxybutane obtained by the hydrogenation of diacetoxybutene is important as an intermediate starting material for butanediol and tetrahydrofuran which are useful as solvents. It is known that diacetoxybutane may be prepared by the hydrogenation of diacetoxybutene in the presence of a palladium or nickel catalyst. The latter compound may be produced by reacting butadiene with acetic acid and oxygen, (British Pat. No. 1,170,222). When utilizing this hydrogenation reaction on an industrial scale, it is very important to keep the reaction temperature within a prescribed range. Since the reaction is exothermic and the temperature region suitable for effecting it is comparatively narrow, this becomes a difficult task and represents a major disadvantage.

Diluting the concentration of diacetoxybutene with a solvent has been used in the past for controlling the hydrogenation reaction temperature. However, this method is not particularly attractive because a large amount of solvent is required and additional steps, such as recovery of the solvent after the reaction, product refining, or the like, become necessary. Consequently, it would be most desirable to have a process for hydrogenation of diacetoxybutene free from the above-described disadvantages.

SUMMARY OF THE INVENTION

Accordingly, one object of the present invention is to provide an industrially useful process for preparing diacetoxybutane by hydrogenating diacetoxybutene in the presence of a supported hydrogenation catalyst wherein contact of the reaction temperature is not a problem.

Briefly, this and other objects of the invention as will hereinafter be made clear by the discussion below have been attained by the process for hydrogenating diacetoxybutene in the presence of a supported hydrogenation catalyst which comprises, catalytically reacting diacetoxybutene with hydrogen continuously in an insulated reaction apparatus comprising a fixed-bed of said hydrogenation catalyst, recirculating some of the gaseous and/or liquid reaction effluent back into the reaction apparatus while controlling the temperature of influx to said reaction apparatus, so as to be lower than the temperature of efflux from said reaction apparatus by 5° to 100° C., thereby keeping the temperature of the hydrogenation reaction apparatus within the specific temperature range. The temperature of the circulating effluent from the reaction apparatus is controlled by an exterior circulating cooling system.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawings, wherein.

DETAILED DESCRIPTION OF THE PREFERRED EMBODIMENTS

Figure 1:
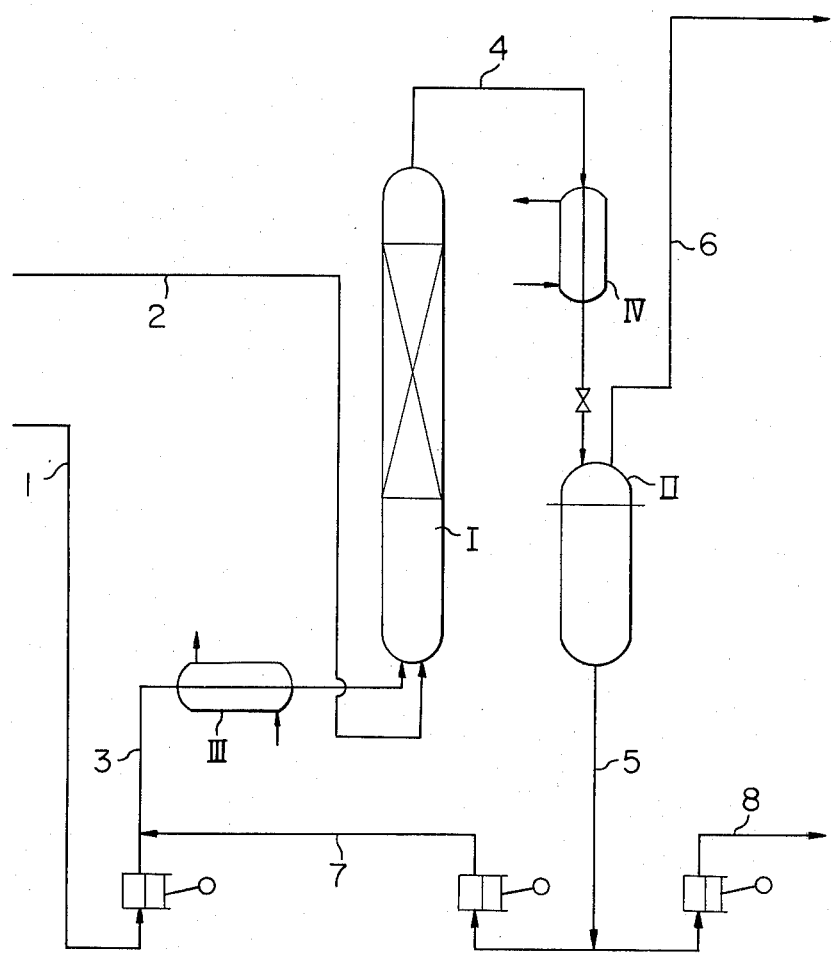
FIG. 1 contains a flow-diagram depicting one embodiment of the reaction process of the invention.

The reactant diacetoxybutene used in the process of the present invention is obtained by reacting butadiene with acetic acid and molecular oxygen in the presence of a palladium catalyst, in some cases in the presence of a solvent. The acetoxylation reaction per se may be carried out according to any known method. In general, butadiene is reacted with acetic acid and oxygen or an oxygen containing gas in the presence of a palladium catalyst incorporated in the form of a fixed-bed, a fluidized-bed, a suspension catalyst system or the like.

Suitable catalysts used in the acetoxylation reaction include a homogeneous liquid catalyst of a palladium salt and a redox agent, such as copper salt, or a solid catalyst comprising a metal or metallic salt of palladium, platinum, rhodium, iridium and ruthenium, in some cases together with a promoter, such as a metal or metallic salt of copper, silver, zinc, nickel, chromium, iron, cobalt, cadmium, tin, lead, molybdenum, tungsten, antimony, tellurium, selenium, bismuth, an alkali metal or an alkaline earth metal.

One preferred example is a catalyst comprising palladium metal and at least one promoter metal such as bismuth, selenium, antimony and tellurium, supported on a carrier. Suitable catalyst carriers include, for example, activated carbon, silica gel, silica alumina, alumina, clay, bauxite, magnesia, diatomaceous earth, pumice or the like.

The concentration of metals on the carrier is generally selected to be 0.1 to 20% by weight for palladium metal, and 0.01 to 30% by weight for the other promoter metal.

The reaction is generally carried out within the temperature range of 40° to 180° C., preferably 60° to 150° C., under a pressure higher than atmospheric pressure.

Suitable reactants for the present invention include mixtures of diacetoxybutenes obtained by separating water, acetic acid, high boiling substances and catalysts from the acetoxylation reaction products obtained as described hereinbefore, or isomers of diacetoxybutene, that is, 1,4-diacetoxy-2-butene or 3,4-diacetoxy-1-butene mutually separated by distillation.

Therefore, these raw materials comprise 1,4-diacetoxy-2-butene or 3,4-diacetoxy-1-butene or mixtures thereof as a main constituent. If circumstances require, a relatively small amount of acetic acid may be mixed (preferably below 10%, by weight). Other high boiling substances can be incorporated only insofar as they do not contaminate the acetoxylation catalyst.

Hydrogen used in the present hydrogenation reaction need not be pure but may be diluted with an inert gas, saturated hydrocarbons, and the like. In this case the hydrogen content should generally be above 10% by volume, preferably above 50% by volume, although the content is not particularly limited. As a source of hydrogen, in addition to ordinary electrolysis hydrogen and reformer hydrogen, a portion of the gas exhausted from the hydrogenation system itself may be used. The exhausted gas in question may include the effluent gas from the hydrogenation apparatus and the gaseous phase left after the vapor-liquid separation of the reaction product liquid.

Suitable hydrogenation catalysts used in the reaction include all known supported palladium or nickel catalysts. The form of the palladium or nickel is not particularly limited. In general palladium metal supported on activated carbon, alumina, magnesia, or the like is used although there are many other kinds of palladium catalysts which can be used. Suitable nickel catalysts include nickel metal of Raney nickel, reduced nickel, or the like, alone or together with a promoter of zinc, vanadium, iron, cobalt, calcium, titanium, bismuth, or the like supported on a carrier. Suitable carriers include generally active carbon, alumina, silica gel, silica-alumina, clay, bauxite, magnesia, diatomaceous earth, pumice or the like. The amount of relevant metal is usually about 0.1–~10%, by weight. Preferred examples are palladium catalysts, especially those supported on active carbon or on alumina.

The hydrogenation is carried out in an insulation type apparatus containing a fixed-bed filled with these catalysts. The reaction can be carried out in a parallel-current flow system in which raw material diacetoxybutene, circulated effluents and hydrogen are flowed upwards or downwards. Alternatively, a vapor-liquid parallel-current flow system, or a counter-current flow system in which the liquid materials such as the reaction products and diacetoxybutene are flowed downwards and the gaseous materials such as hydrogen and circulated gaseous effluent are flowed upwards in order to contact therewith, can be used.

The hydrogenation reaction is carried out within the temperature range of room temperature to 200° C., preferably from 50° to 150° C. When the temperature is lower than room temperature, sufficient reaction velocity cannot be obtained and a wasteful amount of catalyst is required. On the other hand, when it is too high, the reaction velocity of the side reactions such as hydrocracking increase thereby decreasing the selectivity of the diacetoxybutane.

The reaction pressure is generally 1 to 400 atm, preferably 1 to 100 atm, although it is not particularly limited. When the pressure is too low, the reaction velocity is not only slow but also the hydrocracking reaction proceeds predominantly. Thereby the selectivity of the diacetoxybutanes decreases. On the other hand, when the reaction pressure is excessively high, among other things, expensive reaction apparatus is required, thereby making the process economically disadvantageous.

In carrying out the present reaction a solvent is not required although it may be used. Suitable solvents include typically saturated aliphatic hydrocarbons, alcohols, ethers, esters, and the like. However, the selection is not limited to these.

The present invention will be illustrated in more detail by reference to FIG. 1 showing a flow diagram of one embodiment.

In FIG. 1, (I) represents a reaction vessel, (II) a vapor-liquid separator, (III) a heater and (IV) a cooler. The type of reaction vessel is not particularly limited. It can be an insulation type reaction vessel provided with a fixed-bed. The hydrogenation catalyst as described above is filled into the reaction vessel. The raw material diacetoxybutene is introduced through the conduit (1). It is then mixed with the liquid circulated to the reaction vessel through the conduit (7) and, after being heated to the prescribed temperature in the heater, is supplied to the bottom of reaction vessel (I).

Hydrogen gas is supplied to the reaction vessel through the conduit (2). Diacetoxybutenes are preferably supplied to the reaction vessel after mixing with the circulating liquid as described above. But the raw materials may be supplied unmixed. The fresh hydrogen-containing gas is supplied directly to the reaction vessel. However, the gaseous effluent withdrawn from the reaction vessel or the gaseous phase remaining after the vapor-liquid separation of the reaction product can be advantageously mixed with the new-feed hydrogen. Such reuse adds to the economy of the reaction. The reaction product withdrawn from the reaction vessel (I) is transferred through the conduit (4) to the cooler (IV) and, after being condensed, is sent to the vapor-liquid separator (II). The gaseous phase emanating from this step may be transferred to an off-gas treating system through the conduit (6) or may be reused as a hydrogen source as described above.

On the other hand, the liquid passes through conduit (5). Part of it is circulated through conduit (7), from which it passes to the reaction vessel after having its temperature adjusted to the prescribed range, hereinafter specified. The remainder is transferred to a refining system through the conduit (8) for recovery of the product.

Other possible embodiments of the present invention include:

(1) In a process for carrying out hydrogenation of diacetoxybutene in an insulation type reactor having a fixed-bed of an hydrogenation catalyst, the reaction effluent withdrawn continuously from the reactor, without vapor-liquid separation and with or without cooling, is circulated back into the reactor. The effluent can be cycled as is or as a mixture with hydrogen and/or a fresh raw diacetoxybutene. The influx temperature of the circulated materials is controlled to be within the prescribed temperature range, whereby the inner temperature of the hydrogenation reactor is maintained in the desired range.

(2) In a process according to above mentioned process (1), the reaction effluent is subjected to a vapor-liquid separation with or without cooling. At least a part of the liquid phase thus obtained is circulated as it is or as a mixture with fresh diacetoxybutene after adjusting the temperature thereof as specified hereinafter.

(3) In a process according to above mentioned process (1), the reaction effluent is subjected to a vapor-liquid separation with or without cooling. At least a part of the liquid phase thus obtained is degassed by reducing the pressure below the reaction pressure. It is then circulated as it is or as a mixture with fresh diacetoxybutene. The temperature of the circulated liquid is adjusted to the temperature hereinafter specified.

(4) In a process according to above mentioned process (3), the reaction effluent is subjected to a vapor-liquid separation with or without cooling. At least a part of the gaseous phase thus obtained is circulated to the reactor as it is or after reducing the pressure below the reaction pressure.

(5) In a process for carrying out hydrogenation of diacetoxybutene in an insulation type reactor having a fixed-bed of an hydrogenation catalyst, at least a part of the gaseous phase withdrawn from the reactor, as it is or after reducing the pressure below the reaction pressure, is cooled to the temperature hereinafter prescribed and circulated to the reactor.

According to the present invention, the temperature of the circulated gaseous or liquid effluent must be within a specific range when it enters the reaction vessel. For this purpose, the temperature of the efflux gas or liquid from the reaction vessel has to be controlled so that the temperature of the influx thereto is lower than that of efflux by 5° to 100° C., preferably 5° to 50° C.

In the case where the raw materials are supplied to the reaction vessel in a manner of vapor-liquid downward parallel-current flow, the vapor and liquid relevant to the reaction are separated at the bottom of the reaction vessel. After controlling the temperature thereof appropriately by means of a cooler, etc., they are circulated to the reaction vessel by means of pump, etc. The amount of reaction effluent circulated is selected within the range of 0.1 to 100 parts by weight, preferably 0.5 to 20 parts by weight, per 1 part of reaction product withdrawn from the reaction vessel for refining.

The circulating liquid is supplied to the reaction vessel with or without mixing with raw material diacetoxybutenes. At this time, it may be divided and introduced to the reaction vessel at several places.

As described above, according to the present invention, the reaction temperature can be effectively controlled by adjusting a part of the reaction effluent within a specific temperature range and circulating it to the reaction zone. Consequently, the reaction advantageously proceeds without undesirable side reactions.

Having generally described the invention, a more complete understanding can be obtained by reference to certain specific examples, which are included for purposes of illustration only and are not intended to be limiting unless otherwise specified.

EXAMPLE 1

870 g of hydrogenation catalyst were filled into a reaction vessel made of SUS 304 of 27.2 mm inner diameter and 2,300 mm in length.

The catalyst was palladium (2% by weight, relative to the carrier) supported on γ-alumina in the shape of a cylinder of 3 mm in diameter and 3 mm in length. Its bulk specific gravity was 0.98 Kg/l.

Diacetoxybutene used as a raw material for the reaction was obtained by distilling the reaction product obtained by catalytically reacting butadiene, acetic acid and an oxygen containing gas with a palladium catalyst. It contained greater than 98% of 1,4-diacetoxy-2-butene.

86 g/hour of diacetoxybutene were mixed with 775 g/hour of circulated reaction product liquid. The mixture was heated to 85° C. by a preheater and supplied to the bottom of the reaction vessel maintained at the pressure of 4.0 Kg/cm$^2$.G. At the same time, hydrogen (above 99.9% in purity) was supplied to the bottom of the reaction vessel at the rate of 200 Nl/hour.

As a result, the temperature of the reaction effluent liquid emanating from the top of the reaction vessel was 115° C. 1,4-diacetoxybutane was obtained with a conversion of 1,4-diacetoxybutene of 91.7% and a selectivity of 1,4-diacetoxybutane of 98.8%.

EXAMPLE 2

Example 1 was repeated in the same manner with the exception of using a mixture containing 70% by weight of 3,4-diacetoxy-1-butene with the balance comprising 1,4-diacetoxy-2-butene as the raw material source of diacetoxybutene. As a result, the temperature of the reaction liquid at the outlet of the reaction vessel was 113° C. The conversion of 3,4- and 1,4-diacetoxybutene was 86.2% and the selectivity of 3,4- and 1,4-diacetoxybutane was 97.5%.

EXAMPLE 3

Figure 2:
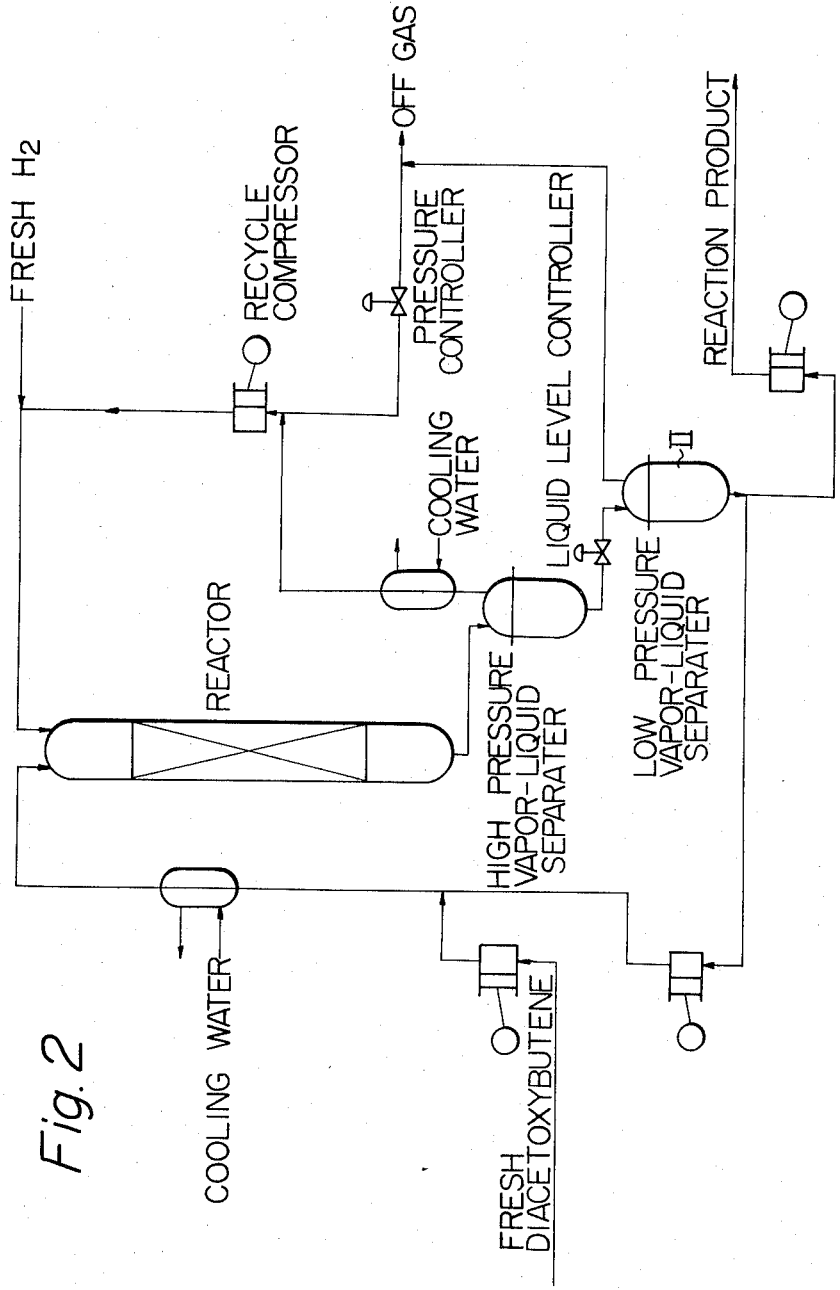
FIG. 2 contains a flow-diagram of a second such embodiment.

According to the process illustrated in FIG. 2, a hydrogenation reaction was carried out. 450 g of hydrogenation catalyst were packed into the reactor made of SUS 316 of 27.2 mm in inner diameter and 2,300 mm in length. The catalyst was palladium (0.5% by weight, relative to the carrier) supported on active carbon in the shape of a cylinder of 3 mm in diameter and 3 mm in length. Its bulk specific gravity and surface area were 0.45 Kg/l and 700 m$^2$/g., respectively.

The diacetoxybutene and hydrogen used as the raw materials were the same as in Example 1. 690 g/hour of diacetoxybutene were mixed with 8,700 g/hour of circulated reaction product liquid. The mixture was cooled to 70° C. by a cooler and fed to the top of the reactor maintained at the pressure of 90 Kg/cm$^2$.C. At the same time, 3.6 Nm$^3$/hour of fresh hydrogen was mixed with 4.5 Nm$^3$/hour of circulated hydrogen. The mixture was cooled to 70° C. and fed to the top of the reactor.

In this case, the superficial liquid linear velocity (LLV) and the superficial gas linear velocity (GLV) were 1.6 m/hour and 200 m/hour, respectively.

Hydrogenation was carried out by supplying hydrogen downwardly, while trickling diacetoxybutene downwardly over the fixed-bed of the catalyst, i.e., in the manner of the trickling phase method.

As a result, the temperature of the reaction liquid withdrawn from the reactor was 86° C. The conversion of 1,4-diacetoxy-2-butene was 98.3% and the selectivity towards 1,4-diacetoxybutane was 97.3%.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. In a process for preparing diacetoxybutane by admitting feed material containing diacetoxybutene into an insulated reaction vessel containing a fixed-bed hydrogenation catalyst, continuously hydrogenating said diacetoxybutene over said catalyst at a temperature of room temperature–200° C., continuously withdrawing a reaction effluent from said reaction vessel and recovering the product diacetoxybutane therefrom, the improvement comprising:

circulating a portion of said withdrawn effluent, with or without gaseous phase-liquid phase separation, in an amount of 0.1 to 100 parts by weight per part of said effluent from which diacetoxybutane is recovered to the inlet of said reaction vessel to mix with the feed material, said portion to be circulated being cooled either prior to or after mixing with said feed material; and controlling the temperature of the feed mixture so that the temperature of the feed mixture is 5°–100° C. less than the temperature of said withdrawn effluent, thereby maintaining the temperature of the hydrogenation within said range.

2. The process of claim 1, wherein at least a part of the reaction effluent is recirculated without gaseous-phase-liquid-phase separation.

3. The process of claim 2, wherein said reaction effluent is recirculated together with fresh hydrogen or diacetoxybutene.

4. The process of claim 1, wherein the reaction effluent is subjected to gaseous-phase-liquid-phase separation and at least a part of the liquid phase thus obtained is recirculated with or without fresh diacetoxybutene.

5. The process of claim 4, wherein the reaction effluent is subjected to gaseous phase-liquid phase separation, the liquid phase thus obtained is degassed by reducing the pressure and at least a part of the degassed liquid is circulated with or without fresh diacetoxybutene.

6. The process of claim 3, wherein at least a portion of the resultant gas phase is circulated as it is or after having its pressure reduced below the reaction pressure.

7. The process of claim 1 wherein the hydrogenation catalyst is a palladium catalyst.

8. The process of claim 1, wherein the temperature of said mixed feed material is less than that of said withdrawn reaction effluent by 5°–50° C.

9. The process of claim 1, wherein the amount of the liquid phase circulated is within the range of 0.1 to 100 parts by weight per one part by weight of the liquid effluent from which diacetoxybutane is recovered.

10. The process of claim 9, wherein the amount of the liquid phase circulated is within the range of 0.5 to 20 parts by weight per one part of the liquid effluent from which diacetoxybutane is recovered.

* * * * *